United States Patent [19]

Cavero et al.

[11] Patent Number: 4,983,598
[45] Date of Patent: Jan. 8, 1991

[54] PHARMACEUTICAL COMPOSITION CONTAINING DILTIAZEM AND ANGIOTENSIN-CONVERTING ENZYME INHIBITOR

[75] Inventors: Icilio Cavero, Creteil; Francois Elkik, Paris; Peter Hicks, Cachan; Jean-Claude Muller, Morsang S/Orge, all of France

[73] Assignee: Synthelabo, Paris, France

[21] Appl. No.: 195,151

[22] Filed: May 18, 1988

Related U.S. Application Data

[63] Continuation-in-part of Ser. No. 115,315, Nov. 2, 1987, abandoned.

[30] Foreign Application Priority Data

Nov. 20, 1986 [FR] France .................................. 86 16138

[51] Int. Cl.$^5$ ...................... A61K 31/40; A61K 31/55
[52] U.S. Cl. ...................................... 514/211; 514/423
[58] Field of Search ................................ 514/211, 423

[56] References Cited

U.S. PATENT DOCUMENTS

| 3,562,257 | 2/1971 | Kugita et al. | 514/929 |
| 4,046,889 | 9/1977 | Ondetti et al. | 514/210 |
| 4,694,002 | 9/1987 | Floyd et al. | 514/211 |
| 4,871,731 | 10/1989 | Walker | 514/423 |

OTHER PUBLICATIONS

Zema, *Clin. Res.*, 32(3), 68CA (1984).
Tomita et al.; *Kekvu to Juntian*, vol. 33 ·10, pp. 1257–64 (1985) pp. 1–14 Engl. Tranol.
Abramowicz et al.; The Medical Letters ® in Drugs & Therapeutics, pp. 107–112 (1985) vol. 26.

*Primary Examiner*—Allen J. Robinson
*Attorney, Agent, or Firm*—Wegner, Cantor, Mueller & Player

[57] ABSTRACT

Compositions of diltiazem and angiotensin-converting enzyme inhibitor useful for the treatment of hypertension, cardiac insufficiency and coronary insufficiency.

2 Claims, No Drawings

PHARMACEUTICAL COMPOSITION CONTAINING DILTIAZEM AND ANGIOTENSIN-CONVERTING ENZYME INHIBITOR

This application is a continuation-in-part of application Ser. No. 115,315 filed Nov. 2, 1987, now abandoned.

BACKGROUND OF THE INVENTION

The present invention relates to pharmaceutical compositions containing diltiazem and an angiotensin-converting enzyme inhibitor useful in the treatment of hypertension.

Hypertension is a field in which polytherapy is encountered extremely frequently.

Calcium inhibitors occupy a position of increasing importance in the field of hypertension. They are being recommended as a first line treatment in elderly hypertensive patients, who are known to be very numerous. It appears, however, that combinations of calcium inhibitors with diuretics and/or β-blockers are not completely satisfactory.

According to indication, diltiazem is beneficial in that it is well tolerated, and is currently gaining as leader in the field of angina pectoris; however, its relatively weak peripheral vasodilatory action could constitute a handicap.

Angiotensin-converting enzyme inhibitors have been found to provide a component having beneficial peripheral vasodilatory action.

SUMMARY OF THE INVENTION

The subject of the present invention is pharmaceutical compositions containing diltiazem and an angiotensin-converting enzyme for the treatment of hypertension, cardiac insufficiency and coronary insufficiency.

Examples of the angiotensin-converting enzyme inhibitors are: captopril, enalapril, alacepril, enalaprilat, fentiapril, lisinopril, ramipril, perindopril, cilazapril, fosinopril, pivopril, quinilapril and zofenopril.

The action of the combinations of diltiazem and angiotensin-converting enzyme inhibitors on hypertension have been studied on unanesthetized spontaneously hypertensive rats (SHR).

The test used in the study is as follows: A catheter is permanently installed in the caudal artery of 12-month old male SHR's under mild ether anaesthesia. The animals are then placed in individual cages which enable them to move freely, and the catheters are connected to Statham P23Gc pressure cells. A special device (Lavasseur J. E., Funk F. C., Patterson J. L. Jr., Physiological pressure transducer for microcirculatory studies. J. Appl. Physiol. 27: 422,425, 1969) permits continuous intra-arterial perfusion of isotonic sodium chloride solution (0.1 ml/kg/min) throughout the experiment, this perfusion preventing possible coagulation without edifying the animals' blood pressure or heart rate. The blood pressure is recorded continuously on a Grass polygraph (model 7D) using a Grass preamplifier (model 7P1).

The results of the tests cited hereinafter have enabled the useful properties of the invention in the treatment of hypertension.

The subject of the invention is compositions having usefulness in the treatment of hypertension, cardiac insufficiency and coronary insufficiency characterized in that they contain a combination of diltiazem and an angiotensin-converting enzyme inhibitor.

The experiments are described in the following examples.

EXAMPLE 1

After a stabilization period of approximately 2 hours, three different groups of animals receive orally a dose of diltiazem (25 mg/kg), a dose of the angiotensin-converting enzyme inhibitor, captopril (20 mg/kg) or a combination of the two doses of diltiazem and captopril. The mean arterial pressure (MAP) is measured before the administration of the therapeutic agents, and then at several times during the 4 hours following the administration of one of the compounds or the combination of the two therapeutic agents.

The results are given in the form of mean decreases in blood pressure with respect to the base-line pressure.

The results obtained for the compounds administered alone and for the combination of diltiazem and captopril are given in the following table.

| Compound | dose mg/kg p.o. | n | Initial MAP mmHg | Δ MAP (mmHg) 0,5 h | 1 h | 1,5 h | 2 h | 3 h | 4 h |
|---|---|---|---|---|---|---|---|---|---|
| diltiazem (dilt) | 25,0 | 5 | 209 ± 4,3 | −15 ± 3,2 | −9 ± 2,5 | −4 ± 3,3 | −2 ± 5,8 | 0 ± 5,2 | 1 ± 5,8 |
| captopril (cap) | 20,0 | 5 | 203 ± 4,1 | −19 ± 2,5 | −17 ± 2,6 | −19 ± 2,5 | −19 ± 2,9 | −18 ± 1,2 | −13 ± 2,6 |
| dilt + cap | 25/20 | 6 | 214 ± 3,8 | −48 ± 3,8* | −41 ± 3,3* | −38 ± 2,1* | −32 ± 4,8 | −24 ± 5,4 | −23 ± 5,9 |

*significantly different from the sum of the effects of diltiazem and captopril given alone.

EXAMPLE 2

After a stabilization period of approximately 2 hours, different groups of animals received orally diltiazem (25 mg/kg) or placebo (distillated water +0.2 % tween) 10 min after intra-arterial administration of saline or of the angiotensin-converting enzyme inhibitor, enalapril (1 mg/kg). The mean arterial pressure (MAP) is measured before the administration of the therapeutic agents, and then at several times during the 4 hours following the administration of one of the compounds or the combination of the two therapeutic agents.

The results are given in the form of mean decreases in blood pressure with respect to the base-line pressure.

The results obtained for the compounds administered alone and for the combination of diltiazem and enalapril are given in the following table.

| Compound | Initial MAP | Δ MAP (mmHg) 0,5 h | 1 h | 1,5 h | 2 h | 3 h | 4 h |
|---|---|---|---|---|---|---|---|
| saline + DTZ$_{25}$ (n = 8) | 194 ± 4,6 | −26 ± 2,6 | −18 ± 1,9 | −13 ± 2,3 | −7 ± 1,9 | −4 ± 1,8 | −1 ± 1,5 |

-continued

| Compound | Initial MAP | Δ MAP (mmHg) | | | | | |
|---|---|---|---|---|---|---|---|
| | | 0,5 h | 1 h | 1,5 h | 2 h | 3 h | 4 h |
| ENA$_1$ + PLACEBO (n = 4) | 194 ± 11,4 | −9 ± 4,3 | −13 ± 3,2 | −9 ± 1,3 | −5 ± 2,0 | −4 ± 1,3 | −3 ± 1,4 |
| ENA$_1$ + DTZ$_{25}$ (n = 8) | 190 ± 4,1 | −40 ± 3,3 | −36 ± 2,6 | −35* ± 2,3 | −33* ± 2,7 | −31* ± 3,0 | −24* ± 2,7 |

*significantly different from the sum of the effects of diltiazem and enalapril given alone.
ENA$_1$ = enalapril (1 mg/kg i.a.)
DTZ$_{25}$ = diltiazem (25 mg/kg p.o.)

EXAMPLE 3

After a stabilization period of approximately 2 hours, different groups of animals receive orally diltiazem (25 mg/kg) or placebo (distillated water +0.2% tween) 30 mn after intra-arterial administration of saline or of the angiotensin-converting enzyme inhibitor, fosinopril (10 mg/kg).

The mean arterial pressure (MAP) is measured before the administration of the therapeutic agents, and then at several times during the 5 hours following the administration of one of the compounds or the combination of the two therapeutic agents.

The results are given in the form of mean decreases in blood pressure with respect to the base-line pressure.

The results obtained for the compounds administered alone and for the combination of diltiazem and fosinopril are given in the following table.

| Compound | MPA Initial Data | Δ MPA (mmHg) | | | | | | |
|---|---|---|---|---|---|---|---|---|
| | | 0,5 h | 1 h | 1,5 h | 2 h | 3 h | 4 h | 5 h |
| SALINE + DTZ$_{25}$ (n = 6) | 193 ± 4,4 | −22 ± 4,2 | −11 ± 4,0 | −9 ± 3,3 | −3 ± 3,8 | −2 ± 4,0 | −2 ± 4,4 | −2 ± 4,2 |
| FOS$_{10}$ + PLACEBO (n = 3) | 195 ± 7,6 | 10 ± 5,8 | 8 ± 3,3 | 7 ± 4,4 | 7 ± 4,4 | 5 ± 2,9 | −3 ± 6,0 | −2 ± 3,2 |
| FOS$_{10}$ + DTZ$_{25}$ (n = 5) | 196 ± 4,3 | −22 ± 3,4 | −25* ± 4,2 | −32* ± 4,1 | −35* ± 5,0 | −36* ± 4,3 | −41* ± 4,0 | −43* ± 4,1 |

*significantly different from the sum of the effects of diltiazem and fosinoril given alone.
DTZ$_{25}$ = diltiazem (25 mg/kg p.o.)
FOS$_{10}$ = fosinopril (10 mg/kg i.a.).

The results show that the combinations of diltiazem and captopril, diltiazem and enalapril, diltiazem and fosinopril, produce a significantly greater antihypertensive effect than the sum of the effects brought about by each of the compounds administered separately.

There is hence, a synergy between the antihypertensive effects of diltiazem and of the angiotensin-converting enzyme inhibitors mentioned above, per unit dose.

Pharmaceutical compositions of the invention may be presented in any form suitable for oral or parenteral administration, in combination with any suitable excipient.

Each unitary dose of the pharmaceutical compositions of the invention contains from 10 to 360 mg of diltiazem and 1 to 100 mg of an angiotensin-converting enzyme inhibitor mentioned above.

The dosage which can be administered daily is such that from 10 to 240 mg diltiazem and from 1 to 100 mg of one of the angiotensin-converting enzyme inhibitors are administered.

What is claimed is:

1. A pharmaceutical composition containing a combination of 10–360 mg of diltiazem and 1–100 mg of an angiotensin-converting enzyme inhibitor, enalapril useful for the treatment of hypertension, cardiac insufficiency, and coronary insufficiency, such that the antihypertensive effect observed upon combined administration of diltiazem and said angiotensin-converting enzyme inhibitor is greater than the sum of the individual anti-hypertensive effects observed upon the separate administration of diltiazem and said angiotensin-converting enzyme inhibitor alone.

2. A method for treatment of hypertension, cardiac insufficiency or coronary insufficiency comprising administering to a subject suffering therefrom a pharmaceutical composition containing a combination of 10 to 360 mg of diltiazem and 1 to 100 mg of an angiotensin-converting enzyme inhibitor, enalapril, such that the anti-hypertenive effect observed upon administration of the combined administration of diltiazem and said angiotensin-converting enzyme inhibitor is greater than the sum of the individual anti-hypertensive effects observed upon the separate administration of diltiazem and said angiotensin-converting enzyme inhibitor alone.

* * * * *